United States Patent [19]

Shaffar

[11] Patent Number: 4,743,561

[45] Date of Patent: * May 10, 1988

[54] LUMINESCENT ASSAY WITH A REAGENT TO ALTER TRANSMITIVE PROPERTIES OF ASSAY SOLUTION

[75] Inventor: Mark R. Shaffar, North Chicago, Ill.

[73] Assignee: Abbott Laboratories, Abbott Park, Ill.

[*] Notice: The portion of the term of this patent subsequent to Jan. 22, 2002 has been disclaimed.

[21] Appl. No.: 708,472

[22] Filed: Mar. 5, 1985

[51] Int. Cl.$^4$ .................... C12Q 1/66; C12Q 1/28; G01N 21/76; G01N 33/53
[52] U.S. Cl. ........................ 436/501; 435/8; 435/16; 435/17; 435/25; 435/26; 435/28; 436/71; 436/79; 436/88; 436/95; 436/97; 436/98; 436/105; 436/108; 436/124; 436/132; 436/172; 436/537; 436/805; 436/909
[58] Field of Search ............... 435/8, 25, 28, 16, 17, 435/26; 436/164, 172, 501, 517, 536, 537, 805, 909, 71, 79, 88, 95, 97, 98, 105, 108, 124, 132

[56] References Cited

U.S. PATENT DOCUMENTS

| | | | |
|---|---|---|---|
| 3,996,345 | 12/1976 | Ullman et al. | 436/815 |
| 4,220,450 | 4/1978 | Maggio | 436/537 |
| 4,372,745 | 2/1983 | Mandle et al. | 436/537 |
| 4,495,293 | 1/1985 | Shaffar | 436/800 |
| 4,604,364 | 8/1986 | Kosak | 436/172 |

FOREIGN PATENT DOCUMENTS 0140641  8/1983  Japan ......................... 435/7

Primary Examiner—Sidney Marantz
Assistant Examiner—David A. Saunders
Attorney, Agent, or Firm—Robert W. Stevenson; Martin L. Katz

[57] ABSTRACT

An improved method and reagents are disclosed for determining a ligand in an assay solution containing the ligand, a reagent system and a luminescent compounds, wherein the intensity of the light emitted by the assay solution is related to the change in the transmittive properties of the assay solution produced by the interaction of the ligand to be determined and a reagent system capable of producing a change in the transmittive properties of the assay solution in the presence of the ligand.

6 Claims, No Drawings

LUMINESCENT ASSAY WITH A REAGENT TO ALTER TRANSMITIVE PROPERTIES OF ASSAY SOLUTION

BACKGROUND OF THE INVENTION

Conventional nonisotopic methods of analysis in the field of clinical medical diagnostics involve the spectrophotometric or fluorometric determination of clinically significant substances, hereinafter referred to as ligands. Such methods are highly sensitive and specific and rely upon the measurement of the change in the optical properties, that is, the transmittive or fluorescent properties of an assay solution resulting from the presence of a particular ligand in the assay solution.

In a spectrophotometric assay, the interaction in an assay solution between the ligand to be determined and a reagent system specific for the ligand, produces a detectable change in the transmittive properties of the assay solution. The change in the transmittive properties refers to the amount of light absorbed or scattered by an assay solution within a particular wavelength band when a beam of light of known intensity is passed through the assay solution. The change in the transmittive properties of an assay solution is measured by passing monochromatic light having a known intensity through the assay solution and determining the ratio of the intensity of the transmitted or scattered light to the intensity of the incident light. The fact that nearly all ligands either absorb energy of a specific wavelength or interact in an assay solution with a particular reagent system to produce a detectable change in the transmittive properties of the assay solution, has resulted in the development of numerous specific spectrophotometric assays. Spectrophotometric assays which rely upon the measurement of the change in the transmittive properties of an assay solution as a measure of a ligand in the assay solution include, for example, assays wherein there is a change in the color of the assay solution, that is, colorimetric assays and assays wherein there is a change in the turbidity of the assay solution, that is, turbidimetric or nephelometric assays. In a colorimetric assay, the change in the transmittive properties of an assay solution is generally referred to as the absorbance of the assay solution and is dependent upon the change in the color of the assay solution due to the interaction of the ligand to be determined and reagent system specific for the ligand. The absorbance of the assay solution is related to the concentration of the ligand in the assay solution. A colorimetric assay utilizes a chromogenic reagent system capable of interacting in an assay solution with the particular ligand of interest, to produce a detectable change in the transmittive properties, specifically the color, of the assay solution. Numerous chromogenic reagent systems useful in the determination of specific ligands have been developed and are commercially available. The principle of turbidimetric assays is to determine the amount of light scattered or blocked by particulate matter as light passes through an assay solution. In a turbidimetric assay, the ligand of interest interacts with a reagent system specific for the ligand to form a suspension of particles in the assay solution. As a beam of light having a known intensity is passed through an assay solution, the suspension of particles formed by the interaction of the ligand and reagent system, blocks or scatters the incident light thereby reducing the intensity of the light transmitted through the assay solution. The change of the transmittive properties in a turbidimetric assay refers to the decrease in the intensity of the light transmitted through an assay solution and is related to the amount of incident light that is scattered or blocked by the suspension of particles and depends upon the number of particles present and the cross-sectional area of such particles. A nephelometric assay is similar to a turbidimetric assay in that the ligand of interest interacts with a reagent system specific for the ligand to form a suspension of particles in the assay solution. In a nephelometric assay, the change in the transmittive properties of the assay solution is also related to the amount of incident light scattered or blocked by the suspension of particles but unlike a turbidimetric assay wherein the intensity of the light transmitted through the assay solution is measured, the scattered or blocked light is measured at an angle to the light incident to the assay solution. Therefore, in a nephelometric assay the change in the transmittive properties refers to the difference in intensities of light incident to the assay solution and light scattered at an angle to the incident light. Turbidimetric and nephelometric assays are utilized in the analysis of blood, urine, spinal fluid, etc., for the determination of ligands such as proteins wherein there is no comparable colorimetric assay due to the lack of an effective chromogenic reagent system. Yoe and Klimman in *Photoelectric Chemical Analysis*, Vol. II: *Nephelometry*, Wiley and Sons, Inc., New York, 1929, describe various nephelometric assays.

Typically in the fluorometric assay, a ligand in an assay solution is chemically or immunologically transformed into a fluorescent complex or conjugate thereby producing a detectable change in the fluorescent properties of the assay solution. The change in the fluorescent properties of the assay solution is measured by exciting the fluorescent complex or conjugate produced, with monochromatic light of a wavelength within the excitation wavelength band of the fluorescer and measuring the intensity of the emitted light at a wavelength within the emission wavelength band of the fluorescer. The fluorescent intensity of the emitted light is related to the concentration of the ligand. However, the intensity of the fluorescence emitted by the assay solution may be inhibited when the ligand to be determined complexes with nonfluorescent interferences such as proteins or phosphates present in the sample, or when the sample containing the ligand to be determined has sufficient color so to act as a filter and thereby reduce the intensity of the emitted fluorescence. It is well recognized that in order to maximize the sensitivity and specificity of a fluorometric assay, these inhibiting factors if present, must be overcome, either by removal of the nonfluorescent interferences or color producing material prior to the analysis, or by compensating for the presence of such factors using an internal standard added to a second aliquot of sample and carrying out the entire assay procedure using the aliquot containing the internal standard.

U.S. Pat. No. 4,495,293, issued Jan. 22, 1985 and commonly assigned herewith, discloses a method for fluorometrically determining a ligand in an assay solution wherein the intensity of the fluorescence emitted by the assay solution is related to the change in the transmittive properties produced by the interaction of the ligand to be determined and a reagent system capable of producing a change in the transmittive properties of the assay solution in the presence of the ligand.

SUMMARY OF THE INVENTION

The present invention provides an improved method for determining the presence or amount of a ligand in a sample suspected of containing the ligand. The method comprises (a) combining to form an assay solution: (i) the sample, (ii) an effective amount of a luminescent reagent; and (iii) an effective amount of a reagent system which in the presence of the ligand to be determined is capable of providing a change in the transmittive properties of the assay solution within a wavelength band that overlaps the emission wavelength of light emitted by the luminescent reagent; (b) activating the luminescent reagent; and (c) measuring the intensity of light emitted by the assay solution as a measure of the concentration of the ligand in the sample.

The present invention further relates to a novel reagent composition useful for determining the presence or amount of a ligand in a sample suspected of containing the ligand. The reagent composition comprises an effective amount of a reagent system capable of providing a change in the transmittive properties of a solution containing the ligand, and an effective amount of a luminescent reagent having an emission wavelength within the wavelength band associated with the change in the transmittive properties of a solution containing the reagent and ligand.

DETAILED DESCRIPTION OF THE INVENTION

As previously stated, in accordance with the method of the present invention, a ligand in a biological sample is determined by first combining in an assay solution the sample, an effective amount of a luminescent reagent and an effective amount of a reagent system. The luminescent reagent is then activated and the intensity of light emitted by the assay solution is measured as an indication of the concentration of the ligand in the sample. The intensity of the light emitted by the assay solution is proportional to the change in the transmittive properties of the assay solution resulting from the interaction of the ligand and reagent system.

As used herein, the term "change in the transmittive properties of the assay solution" refers to the amount of light absorbed or scattered by an assay solution within a particular wavelength band when a beam of light of known intensity is passed through the assay solution and generally depends upon the change in the color or turbidity of the assay solution. In particular, the change in the transmittive properties refers to the change in the amount of light absorbed or scattered by the assay solution within a particular wavelength band wherein the change results substantially from the interaction of the ligand and a reagent system specific for the ligand. The change in the transmittive properties is generally measured by passing monochromatic light having a known intensity through the assay solution and determining the ratio of the intensity of the transmitted or scattered light to the intensity of the incident light. The change in the transmittive properties, that is, the change in the amount of light absorbed or scattered by the assay solution within a particular wavelength band is proportional to the concentration of the ligand in the assay solution. It has now been found that in an assay solution containing a ligand, reagent system and a luminescent reagent, the change in the transmittive properties, within a wavelength band that overlaps the emission wavelength band of the luminescent reagent resulting from the interaction of the ligand and reagent system, also results in a proportional change in the intensity of the light emitted by the assay solution. Therefore, in accordance with the method of the present invention, the change in the intensity of the luminescent light emitted by the assay solution is proportional to the concentration of the ligand in the assay solution. It should be noted that in accordance with the method of the present invention, the change in intensity of the luminescent light emitted by an assay solution containing the ligand to be determined, reagent system and luminescent reagent, when compared to the intensity of the luminescent light emitted by an assay solution containing only the reagent system and a luminescent reagent, is due entirely to the change in the transmittive properties produced by the interaction of the ligand and reagent system. There is no reaction, either chemical or immunological, between the luminescent reagent and any other component, namely, the ligand to be determined or reagent system, in the assay solution. Therefore, the intensity of the luminescent light emitted by the assay solution does not depend upon the intermolecular distance between the luminescent reagent and any chromogenic substances or suspended particles that may be present in the assay solution.

The ligands determinable by the method of the present invention include clinically significant substances which are capable of being colorimetrically, turbidimetrically or nephelometrically determined. That is, the ligand must be capable of interacting with a reagent system to produce a detectable change in the transmittive properties related to the concentration of the ligand in the assay solution. Representative of ligands that may be assayed in accordance with the method of the present invention include, for example, glucose, uric acid, cholesterol, creatine, lactate, lactate dehydrogenase (LDH), triglycerides, immunoglobulins, cholinesterase, serum glutamate oxalactate transaminase (SGOT), serum glutamate pyruvate transaminase (SGPT), creatine phosphokinase (CPK), ethanol, total protein, albumin, calcium, bilirubin, blood urea nitrogen (BUN), ammonia, magnesium, phosphorous, chloride and the like.

The term "luminescent reagent" refers to a compound or composition having luminescent characteristics related to the transmittive characteristics of a solution containing a reagent system and ligand. In particular, the emission wavelength band associated with the luminescent reagent must lie within the wavelength band associated with the change in the transmittive properties of the assay solution resulting from the interaction of the ligand and the reagent system. In addition, as mentioned there is no chemical or immunological binding between the luminescent reagent and the ligand to be determined or the reagent system. Another consideration concerns the pH of the reagent system. The luminescent reagent must luminesce within the pH range effective for the reagent system to interact with the ligand to be determined. In a colorimetric assay, the emission wavelength band associated with the luminescent reagent must at least partially lie within the absorption wavelength band associated with the interaction of the ligand and chromogenic reagent system. In a turbidimetric or nephelometric assay, the emission wavelength band associated with the luminescent reagent must at least partially lie with the wavelength band wherein the turbidity of an assay solution containing the ligand and turbidimetric or nephelometric reagent system is measured.

A wide variety of luminescent reagents may be employed in the present invention. For example, chemiluminescent, phosphorescent or bioluminescent reagents can be used. The choice of the luminescent reagent will depend upon the particular ligand to be determined and the chromogenic reagent system employed. Representative of the class of luminescent reagent that may be employed include, for example: anthracenes, triphenylbenzenes, diphenyl-napthalenes, perylenes, chrysenes, oxalates, luminols, lophines, lucigenins, luciferins, acridiniums, trans-azodicarboxylates, pyrogallols and coelenterate chromophores. These luminescent reagents can be triggered to product light by using organic compounds such as hydrogen peroxide, potassium ferricyanide, potassium permanganate, metal ions and the like, or by biological catalysts such as luciferase or peroxidase, or by physical means such as changes in temperature, pH or radioactive emissions, e.g. x-rays.

The term "reagent system" as used herein refers to a chemical system containing one or more reagents which in the presence of the ligand of interest produces a change in the band that overlaps the emission wavelength band of a luminescent reagent. Reagent systems effective in the methods of the present invention will depend on the specific ligand to be determined and whether the change in the transmittive properties to be measured is due to the change in the color or turbidity of the assay solution. In a colorimetric assay, that is, wherein the change in color of the assay solution is related to the change in the transmittive properties of the assay solution, a chromogenic reagent system is employed as the reagent system. In a turbidimetric or nephelometric assay wherein the turbidity, that is, the amount of light blocked or scattered by a suspension of particles, is related to the change in the transmittive properties of the assay solution, a turbidimetric reagent system or a nephelometric reagent system, respectively, is employed.

The term "chromogenic reagent system" as used herein, refers to a chemical system containing one or more reagents which will react in accordance with a specific reaction sequence with the ligand to be determined, to product a detectable change in the transmittive properties, in particular the colorimetric properties, of an assay solution within a wavelength band that overlaps the excitation and/or emission wavelength bands of the luminescent reagent. For the purposes of the present invention, the various reagents comprising such chromogenic reagent systems may be added individually or in any combination to the assay solution, unless the order of addition is limited by the particular reaction sequence. Such chromogenic reagent systems utilized for colorimetrically determining ligans are well known in the art. See, for example Henry et al., Clinical Chemistry, Principles and Techniques; New York, Hoeber Medical Division, Haper & Row (1964); Tietz, Fundamentals of Clinical Chemistry, W. B. Saunders Company (1970). Various assay kits and reagent systems are commercially available and employ standard techniques and reagents. In general, those colorimetric procedures rely on the principle that a ligand will react with a chromogenic reagent system containing a color producing reagent, to produce a detectable color change in the assay solution. Representative chromogenic reagent systems include for example, oxidase reaction systems, including end point and kinetic determinations, and NADH/NAD reaction systems. For example, an oxidase reaction system utilized oxidative enzymes to react with the ligand to release hydrogen peroxide which subsequently reacts with a dye in the presence of peroxidase to produce a change in the colorimetric properties of the assay solution as an indication of the amount of ligand in the sample. An NADH/NAD reaction system relys upon the reduction of NAD to NADH or the oxidation to NADH to NAD and the subsequent reaction with a dye system to produce a change in the colorimetric properties of the assay solution as a measure of the concentration of ligand in the sample. The term "effective amount of reagent system" as used herein, refers to an amount of reagent system sufficient in the presence of a ligand to produce a detectable change in the colorimetric properties of the assay solution. Such effective amounts are readily ascertained by one of ordinary skill in the art.

The following serves to illustrate some of the various chromogenic reagent systems and the reaction sequences involved which may be utilized in accordance with the method of the present invention. The following abbreviations are utilized herein:

| | |
|---|---|
| DHBS | 3,5-dichloro-2-hydroxybenzene sodium sulfonate |
| AAP | 4-aminoantipyrine |
| HRPO | horseradish peroxidase |
| NAD | oxidized nicotinamide-adenine dinucleotide |
| NADH | reduced nicotinamide-adenine dinucleotide |
| LDH | lactate dehydrogenase |
| SGOT | serum glutamic oxalacetic transaminase |
| SGPT | serum glutamic pyruvic transaminase |
| CPK | creatine phosphokinase |
| INT | 2-(p-iodophenyl)-3-(p-nitrophenyl)-5-phenyltetrazolium chloride |
| ATP | adenosine triphosphate |
| ADP | adenosine diphosphate |
| EGTA | ethyleneglycol-bis($\beta$-aminoethylenether)-N,N'—tetracetic acid |

In addition, because of the uncertainty of the specific structure of the product in some of the following reaction sequences, a product of a particular reaction sequence that produces the color of the assay solution and is measured in a spectrophotometric assay, unless specifically identified, is generally referred to herein as a "chromogen". In reaction sequence 11-16 illustrating NADH/NAD systems, the product that produces the color of the assay solution is formazine. In reaction sequence 21, illustrating an assay for blood urea nitrogen, the product that produces the color of the array solution is indophenol. In reaction sequence 24 illustrating an assay for chloride, the product that produces the color of the assay solution is ferric thiocyanate.

1. Ligand: glucose
    Chromogenic Reagent System:  glucose oxidase
    DHBS
    AAP
    HRPO Reaction Sequence:

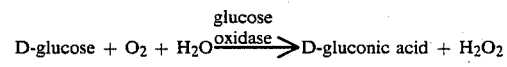

$$2H_2O_2 + DHBS + AAP \xrightarrow{HRPO} chromogen$$

2. Ligand: Uric Acid
   Chromogenic Reagent System: uricase
   DHBS
   AAP
   HRPO Reaction Sequence:

$$Uric\ Acid + O_2 + 2H_2O \xrightarrow{uricase} allantoin + CO_2 + H_2O_2$$

$$2H_2O_2 + DHBS + AAP \xrightarrow{HRPO} chromogen$$

3. Ligand: Cholesterol (Cholesterol and Cholesterol Esters)
   Chromogenic Reagent System: cholesterol esterase
   cholesterol oxidase
   DHBS
   AAP
   HRPO Reaction Sequence:

$$Cholesterol\ esters \xrightarrow{Cholesterol\ esterase} cholesterol$$

$$Cholesterol + O_2 \xrightarrow{Cholesterol\ oxidase} \Delta^4\ cholesterone + H_2O_2$$

$$2H_2O_2 + DHBS + AAP \xrightarrow{HRPO} chromogen$$

4. Ligand: Creatinine
   Chromogenic Reagent System: creatininase
   creatinase
   sarcosine oxidase
   DHBS
   AAP
   HRPO Reaction Sequence:

$$Creatinine + H_2O \xrightarrow{creatininase} creatine$$

$$creatine + H_2O \xrightarrow{creatinase} sarcosine + urea$$

$$sarcosine + H_2O + O_2 \xrightarrow{sarcosine\ oxidase} glycine + HCH{=}O + H_2O_2$$

$$2H_2O_2 + DHBS + AAP \xrightarrow{HRPO} chromogen$$

5. Ligand: Lactate
   Chromogenic Reagent System: NAD
   LDH
   pyruvate oxidase
   DHBS
   AAP
   HRPO Reaction Sequence:

$$Lactate + NAD \xrightleftharpoons{LDH} pyruvate + NADH$$

$$pyruvate + O_2 \xrightarrow{pyruvate\ oxidase} acetylphosphate + CO_2 + H_2O_2$$

$$2H_2O_2 + DHBS + AAP \xrightarrow{HRPO} chromogen$$

6. Ligand: Triglycerides
   Chromogenic Reagent System: lipase
   glycerol kinase
   glycerol phosphate oxidase
   DHBS
   AAP
   HRPO Reaction Sequence:

$$Triglyceride + 3H_2O \xrightarrow{lipase} glycerol + fatty\ acids$$

$$glycerol + ATP \xrightleftharpoons{glycerol\ kinase} glycerol\text{-}3\text{-}phosphate + ADP$$

$$glycerol\text{-}3\text{-}phosphate \xrightarrow{glycerol\ phosphate\ oxidase} dihydroxyacetonephosphate + H_2O_2$$

$$2H_2O_2 + DHBS + AAP \xrightarrow{HRPO} chromogen$$

7. Ligand: Cholinesterase
   Chromogenic Reagent System: acetylcholinesterase
   choline oxidase
   DHBS
   AAP
   HRPO Reaction Sequence:

$$Acetylcholine \xrightarrow{acetylcholinesterase} choline + acetate$$

$$choline + O_2 \xrightarrow{choline\ oxidase} 2H_2O_2$$

$$2H_2O_2 + DHBS + AAP \xrightarrow{HRPO} chromogen$$

8. Ligand: SGOT
   Chromogenic Reagent System: asparate
   α-ketoglutarate
   oxalocetatedecarboxylase
   pyruvate oxidase
   DHBS
   AAP
   HRPO Reaction Sequence:

$$Asparate + \alpha\text{-}ketoglutarate \xrightleftharpoons{SGOT} glutamate + oxaloacetate$$

$$oxaloacetate \xrightleftharpoons{oxaloacetate\ decaboxylase} pyruvate + CO_2$$

$$pyruvate + O_2 \xrightarrow{pyruvate\ oxidase} H_2O_2 + acetylphosphate + CO_2$$

$$2H_2O_2 + DHBS + AAP \xrightarrow{HRPO} chromogen$$

9. Ligand: SGPT
   Chromogenic System: L-alanine
   α-ketoglutarate
   pyruvate oxidase
   DHBS
   AAP
   HRPO Reaction Sequence:

$$Alanine + \alpha\text{-}ketoglutarate \xrightleftharpoons{SGPT} glutamate + pyruvate$$

$$pyruvate + O_2 \xrightarrow{pyruvate\ oxidase} acetylphosphate + H_2O_2 + CO_2$$

$$2H_2O_2 + DHBS + AAP \xrightarrow{HRPO} chromogen$$

10. Ligand: CPK
    Chromogenic System: Creatine phosphate

|   |   |
|---|---|
|   | creatinase |
|   | sarcosine oxidase |
|   | DHBS |
|   | AAP |
|   | HRPO |

Reaction Sequence:

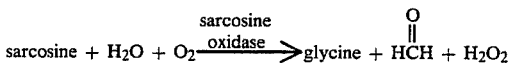

11. Ligand: Ethanol
    Chromogenic Reagent System:  NAD
    alcohol dehydrogenase
    INT
    diaphorase Reaction Sequence:

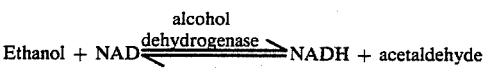

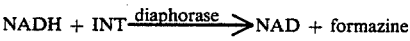

12. Ligand: SGOT
    Chromogenic Reagent System:  asparatate
    α-ketoglutarate
    NAD
    glutamate dehydrogenase
    diaphorase
    INT Reaction Sequence:

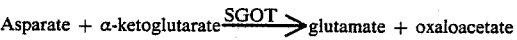

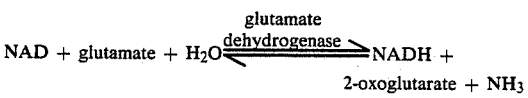

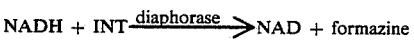

13. Ligand: SGPT
    Chromogenic Reagent System:  L-alanine
    α-ketoglutarate
    NAD
    glutarate dehydrogenase
    diaphorase
    INT Reaction Sequence:

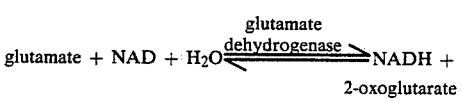

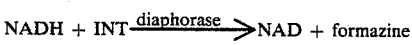

14. Ligand: Glucose
    Chromogenic Reagent System:  ATP
    hexokinase
    NAD
    glucose-6-phosphate
    dehydrogenase
    INT
    diaphorase Reaction Sequence:

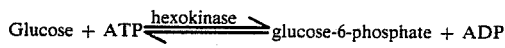

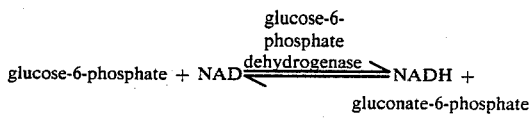

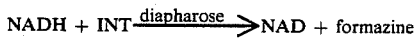

15. Ligand: CPK
    Chromogenic Reagent System:  Creatine phosphate
    ADP
    glucose
    hexokinase
    NAD
    glucose-6-phosphate
    dehydrogenase
    INT
    diaphorase Reaction Sequence:

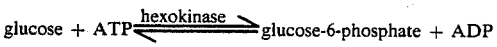

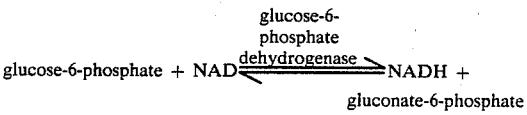

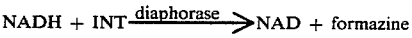

16. Ligand: LDH
    Chromogenic Reagent System:  L-lactate
    NAD
    INT
    diaphorase Reaction Sequence:

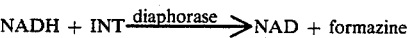

17. Ligand: Total Protein
    Chromogenic Reagent System:  copper tartrate
    sodium tartrate
    lithium acetate
    Reaction Sequence:
    Protein + copper tartrate + sodium tartrate +

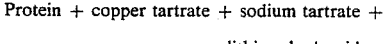

18. Ligand: Albumin
    Chromogenic Reagent System:  bromocreosol green
    Reaction Sequence:

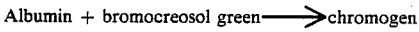

19. Ligand: Calcium
    Chromogenic Reagent System:  o-cresolphthalein complexon
    8-quinolino sulfate
    Reaction Sequence:
    Calcium + o-cresolphthalein +

20. Ligand: Bilirubin
    Chromogenic Reagent System: diazonium salt of 2,4-dichloroaniline
    methanol
    sulfamic acid
    Reaction Sequence:
    Bilirubin + diazonium salt of 2,4-dichloroaniline $\xrightarrow[\text{sulfamic acid}]{\text{methanol}}$ chromogen 21. Ligand: Blood Urea Nitrogen (Urea)
    Chromogenic Reagent System: urease
    sodium hypochorite
    phenol
    sodium hydroxide
    sodium nitroprusside
    Reaction Sequence:

Urea $\xrightleftharpoons{\text{urease}}$ 2NH$_3$ + CO$_2$

2NH$_3$ + 2NaClO $\longrightarrow$ 2NH$_2$Cl + 2NaOH

2NH$_2$Cl + 2 phenol + 2NaOH $\longrightarrow$
    2 p-aminophenol + 2NaCl + 2H$_2$O 2 p-aminophenol + 2 phenol + O$_2$ $\longrightarrow$
    2 indophenol + 2H$_2$O 22. Ligand: Magnesium
    Chromogenic Reagent System: potassium chloride
    calmagite
    potassium cyanide
    potassium hydroxide
    EGTA
    Reaction Sequence:

Magnesium + KCl + calmagite + KCN $\xrightarrow[\text{EGTA}]{\text{KOH}}$ chromogen 23. Ligand: Phosphorous
    Chromogenic Reagent System: molybdic acid
    sulfuric acid
    semidine hydrochloride
    trichloroacetic acid
    Reaction Sequence:
    Phosphate + molybdic acid + sulfuric acid $\xrightarrow[\substack{\text{semidine hydrochloride} \\ \text{trichloroacetic acid}}]{}$ chromogen 24. Ligand: Chloride
    Chromogenic Reagent System: potassium thiocyanate
    mercuric chloride
    perchloric acid
    mercuric perchlorate
    ferric perchlorate
    Reaction Sequence:

2Cl$^-$ + Hg(SCN)$_2$ $\longrightarrow$ HgCl$_2$ + 2SCN$^-$

3SCN$^-$ + Fe$^{++}$ $\longrightarrow$ Fe(SCN)$_3$

The term "turbidimetric reagent system" as used herein refers to a chemical system containing one or more reagents that will interact in accordance with a specific procedure with the ligand to be determined to produce a detectable change in the transmittive properties, in particular the turbidity, of an assay solution within a wavelength band that overlaps the emission wavelength bands of the luminescent reagent. For the purpose of the present invention, the various reagents comprising turbidimetric reagent systems may be added individually or in any combination to the assay solution, unless the order of addition is limited by the particular reaction sequence. Various turbidimetric reagent systems are well known in the art. One important class of assays utilizing a turbidimetric reagent system includes assays to turbidimetrically measure human immunoglobulins. The principle upon which such assay rely is based upon the formation of a specific complex consisting of a suspension of particles, due to the reaction of a turbidimetric reagent system consisting of antiserum specific to the immunoglobulin to be determined, and the immunoglobulin of interest. The suspension of particles due to the formation of an antiserum-immunoglobulin complex produces a change in the turbidity of the assay solution. Therefore, if an excess of antiserum over human immunoglobulin is employees in the assay solution, the light transmitted throught the suspension decreases as the concentration of immunoglobulin the sample increases.

The term "nephelometric reagent system" as used herein refers to a chemical system containing one or more reagents that will interact in accordance with a specific procedure with the ligand to be determined to produce a detectable change in the transmittive properties, in particular the turbidity, of the assay solution, within a wavelength band that overlaps the emission bands of the luminescent reagent nephelometric assays rely upon the same principles as turbidimetric assays except that nephelometric measurements of an assay solution, unlike turbidimetric measurements, measure the scattered light at an angle to the incident light. Numerous turbidimetric and nephelometric assays are known in the art and the reagent systems employed in such assays are readily ascertained by one of ordinary skill in the art.

In carrying out a preferred method of the present invention the assay solution is introduced into a read cell, e.g. of associated, largely conventional analytical instrument such as those hereinafter described. By observing the emission intensity at a particular wavelength, one can relate this intensity to known standards. By carrying out the assay procedure of the present invention with an unknown in substantially the same manner as with standards containing known amounts of the ligand to be determined, a qualitative or quantitative determination of the amount of ligand present in the unknown sample may be achieved.

Although the concentration of ligand which may be determined in accordance with the methods of the present invention depends in a large part upon the specific instrument, such as a luminometer, which is employed, as well as the specific reagent system utilized, samples containing ligands in a concentration range as low as 0.01–0.1 mM have been determined.

The pH of the assay solution is generally dependent upon the specific reagent system employed. The pH of the reagent system will be a factor in the choice of a luminescent reagent in that is is necessary that the luminescent reagent emit light within the pH range of the reagent system.

With certain ligands and luminescent reagents, there may be small but insignificant amounts of nonspecific binding of the ligands and luminescent to proteins. If protein interference is a factor, it is preferred that the protein concentration of the assay solution be minimized by prior treatment of the sample by ultrafiltration, gel filtration, precipitation, dialysis, and the like. In addition, nonspecific binding of the ligands or luminescent reagents employed to proteins may be minimized by the addition of a surfactant such as Triton X-100 or the like, to the assay solution.

The method the present invention is generally conducted within a temperature range from about 15°–40° C., and preferably, from about 25°–40° C. It is also preferred that the assay be conducted at a substantially constant temperature.

The following example serves to illustrate the method of the present invention. The concentration of reagents and other variable parameters are only shown to exemplify the method of the present invention and are not be be considered as limitations thereof.

EXAMPLE

Glucose Assay

A Glucose working reagent was prepared by combining the following solutions before use:
100 ml of 0.2M Glycine pH 7.7
1 ml of 60 mM Adenosine Triphosphate
1 ml of 10 mM D Luciferin
4 ml of a solution containing 2200 4/ 1 glucose oxidase in 0.1M potassium phosphate pH 5
4 ml of a solution containing 400 I.U./ml HRPO and 1 mg/ml of 4-aminoantipyrene
4 ml of a solution containing 5.3 mg/ml 3–5 Dichloro-2-hydroxy benzene sulfonate To 3 ml of the working reagent were added 25 ul of a glucose standard solution. This mixture was allowed to incubate for 3 minutes at ambient temperature, to reach an endpoint color formation. At this time 100 ul of a luciferase solution were added to activate the chemiluminescent reaction. The cuvette was quickly mixed and placed in a Perkin Elmer fluorimeter to measure the peak luminescent signal at 537±14 nm emission with the excitation lamp turned off. Peak heights were then taken off the chart recorder and plotted vis-a-vis glucose concentration.

| Glucose Concentration | Chart Units |
|---|---|
| 0 mg/dl | 41 |
| 100 mg/dl | 21 |
| 300 mg/dl | 9.5 |
| 500 mg/dl | 5.5 |

The reaction scheme for the foregoing Example is as follows:

Glucose Reaction

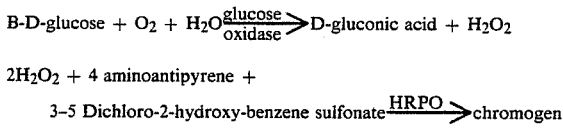

$$\text{B-D-glucose} + O_2 + H_2O \xrightarrow{\text{glucose oxidase}} \text{D-gluconic acid} + H_2O_2$$

$$2H_2O_2 + 4 \text{ aminoantipyrene} +$$

$$\text{3-5 Dichloro-2-hydroxy-benzene sulfonate} \xrightarrow{\text{HRPO}} \text{chromogen}$$

Chemiluminescent Reaction

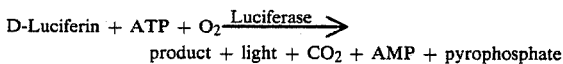

$$\text{D-Luciferin} + \text{ATP} + O_2 \xrightarrow{\text{Luciferase}} \text{product} + \text{light} + CO_2 + \text{AMP} + \text{pyrophosphate}$$

It is apparent from the preceding Example that the method of the present invention is adaptable to a wide variety of assay systems. In addition to providing the capability of determining an unknown ligand utilizing known chromogenic reagent systems by luminescent means, the method of the present invention increases the linearity of an assay employing chromogenic reagent systems. In particular, the method of the present invention increases the linearity ranges of assays at high absorbance values. It is well known that due to instrumentation limitations, the linearity of colorimetric assays decreases substantially at chromogen concentrations having absorbance values greater than 2.0. Using the methods of the present invention, it is possible to extend linearity of an assay using concentrations of reagent system and ligand that result in a chromogen concentration having an absorbance value greater than 2.0.

As previously mentioned, the present invention related to novel reagent compositions which may be utilized to either spectrophotometrically, or by luminescence, measure the concentration of a ligand in an assay solution. Such reagent compositions comprise an effective amount of a reagent system specific for the ligand, that is, a reagent system capable of providing a change in the transmittive properties of a solution containing the ligand to be determined, and effective amount of a luminescent reagent having an emission wavelength band that overlaps the wavelength band associated with the change in the transmittive properties of a solution containing the reagent system and the ligands to be determined. It has been found that the effective amount of luminescent reagent required to produce a reagent composition useful to determine a ligand in accordance with the method of the present invention, does not interfer with the measurement of the transmittive properties of the assay solution. Therefore, an assay solution containing the ligand to be determined and reagent composition of the present invention specific for the ligand, may be spectrophotometrically measured, or measured by luminescence to determine the concentration of the ligand in the assay solution.

Although this invention has been described with respect to a specific embodiment representing a glucose assay system, the details thereof are not to be construed as limitations, for it will be apparent that various equivalents, changes and modifications may be resorted to without departing from the spirit and scope thereof and it is understood that such equivalent embodiments are intended to be included herein. Thus, it is to be appreciated that a wide variety of ligands, such as those represented in the reactio schemes set forth herein, can be assayed utilizing the chromogenic reagent systems disclosed in combination with a luminescent reaction scheme such as that set forth in the Example. Moreover, not only can a luciferin, as specifically set forth in the Example, be used, but also any of the aforementioned luminescent compounds, can be employed usually by direct substitution therefor, as will be apparent to one of ordinary skill in the art given the teachings hereof.

What is claimed is:

1. A method for determining a ligand in a sample suspected of containing the ligand, which method comprises:
   (a) combining to form an assay solution
      (i) said sample;
      (ii) a luminescent reagent;
      (iii) a reagent system which in the presence of the ligand to be determined is capable of providing a change in the transmittive properties of the assay solution within a wavelength band that overlaps the emission wavelength band of light produced by the luminescent reagent;

(b) activating the luminescent reagent; and (c) measuring the intensity of light emitted by the assay solution as a measure of the presence or amount of the ligand in the sample.

2. A method according to claim 1 wherein the reagent system is a chromogenic reagent system or a turbidimetric reagent system.

3. A method according to claim 2 wherein the reagent system is a chromogenic reagent system.

4. A method according to claim 1 wherein the luminescent reagent is chemiluminescent.

5. A method according to claim 1 wherein the luminescent reagent is bioluminescent.

6. A reagent composition useful for determining the presence or amount of a ligand in a sample suspected of containing said ligand, said composition comprising a reagent system capable of providing a change in the transmittive properties of a solution containing said ligand, and a luminescent reagent having an emission wavelength within the wavelength band associated with the change in transmittive properties of a solution containing said reagent and ligand.

* * * * *